United States Patent
Huang et al.

(10) Patent No.: US 9,880,128 B2
(45) Date of Patent: Jan. 30, 2018

(54) ELECTRODE STRIP AND SENSOR STRIP AND MANUFACTURE METHOD THEREOF AND SYSTEM THEREOF

(71) Applicant: APEX BIOTECHNOLOGY CORP., Hsinchu (TW)

(72) Inventors: Ying-Che Huang, Hsinchu (TW); Lan-Hsiang Huang, Taichung (TW); Ching-Yuan Chu, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 375 days.

(21) Appl. No.: 14/640,193

(22) Filed: Mar. 6, 2015

(65) Prior Publication Data

US 2015/0276671 A1    Oct. 1, 2015

Related U.S. Application Data

(62) Division of application No. 13/725,244, filed on Dec. 21, 2012, now Pat. No. 9,039,877.

(30) Foreign Application Priority Data

Jul. 20, 2012    (TW) .............................. 101126157 A

(51) Int. Cl.
*G01N 27/327*    (2006.01)
*G01N 27/416*    (2006.01)
(Continued)

(52) U.S. Cl.
CPC ......... *G01N 27/4166* (2013.01); *C12Q 1/001* (2013.01); *C12Q 1/005* (2013.01);
(Continued)

(58) Field of Classification Search
CPC . G01N 2021/7759; G01N 2035/00108; G01N 27/3272
See application file for complete search history.

(56) References Cited

U.S. PATENT DOCUMENTS 5,264,103 A * 11/1993 Yoshioka ............... C12Q 1/004
204/403.1
6,436,255 B2 * 8/2002 Yamamoto ............. C12Q 1/005
204/403.1
(Continued)

FOREIGN PATENT DOCUMENTS

CN    1991368        7/2007
CN    1991368 A      7/2007
(Continued)

OTHER PUBLICATIONS

Office Action and search report dated Oct. 19, 2015 from the China counterpart application 201210384324.0.
(Continued)

*Primary Examiner* — Alexander S Noguerola
(74) *Attorney, Agent, or Firm* — Muncy, Geissler, Olds & Lowe, P.C.

(57) ABSTRACT

The present disclosure relates to an electrode strip, a sensor strip, a system thereof and a manufacturing method thereof. The sensor strip includes a first reactive film, a second reactive film and a vent hole. The first reactive film includes a substrate, a first electrode layer and a first insulation layer. The first end of the first insulation layer is concaved to a first depth to form a first reactive area. The second reactive film includes a second electrode layer and a second insulation layer. The first end of the second insulation layer is concaved to a second depth to form a second reactive area. The vent hole penetrates the second insulation layer, the second electrode layer and the first insulation layer so as to connect the first reactive area and the second reactive area.

17 Claims, 12 Drawing Sheets

(51) Int. Cl.
 *C12Q 1/00* (2006.01)
 *G01N 33/80* (2006.01)
(52) U.S. Cl.
 CPC ..... *G01N 27/3271* (2013.01); *G01N 27/3273* (2013.01); *G01N 27/3274* (2013.01); *G01N 33/80* (2013.01); *Y10T 156/10* (2015.01); *Y10T 156/1052* (2015.01); *Y10T 156/1057* (2015.01)

(56) References Cited

U.S. PATENT DOCUMENTS

| | | | | |
|---|---|---|---|---|
| 6,830,669 | B2* | 12/2004 | Miyazaki | G01N 27/3272 204/403.01 |
| 7,771,575 | B2* | 8/2010 | Kusaka | B01L 3/502715 204/400 |
| 2002/0100685 | A1 | 8/2002 | Huang et al. | |
| 2003/0064525 | A1* | 4/2003 | Liess | G01N 27/3274 436/149 |
| 2005/0100880 | A1 | 5/2005 | Chang | |
| 2007/0131549 | A1* | 6/2007 | Cai | C12Q 1/006 204/403.02 |

FOREIGN PATENT DOCUMENTS

| | | | |
|---|---|---|---|
| CN | 102033087 A | 4/2011 | |
| EP | 0745843 A2 * | 12/1996 | ........... G01N 27/327 |
| EP | 2 050 824 A1 | 4/2009 | |
| JP | H08-327582 A | 12/1996 | |
| JP | H08327582 | 12/1996 | |
| TW | 201120444 | 6/2011 | |
| TW | 201120444 A | 6/2011 | |
| TW | CN102128932 A | 7/2011 | |

OTHER PUBLICATIONS

English abstract translation of the Office Action dated Oct. 19, 2015 from the China counterpart application 201210384324.0.
English abstract translation of CN1991368.
English abstract translation of TW201120444.
English abstract translation of JPH08327582.
Office Action dated Mar. 9, 2015 from the Chinese counterpart application 201210384324.0.
Search report dated Mar. 9, 2015 from the Chinese counterpart application 201210384324.0.
English abstract translation for Office Action dated Mar. 9, 2015 from the Chinese counterpart application 201210384324.0.
English abstract translation of CN1991368 (A).
English abstract translation of TW201120444 (A).
English abstract translation of CN102128932 (A).
English abstract translation of JPH08327582 (A).
Office Action dated Apr. 18, 2016 from the China counterpart application 201210384324.0.
English abstract translation of the Office Action dated Apr. 18, 2016 from the China counterpart application 201210384324.0.
English abstract translation of CN102033087 (A).

* cited by examiner

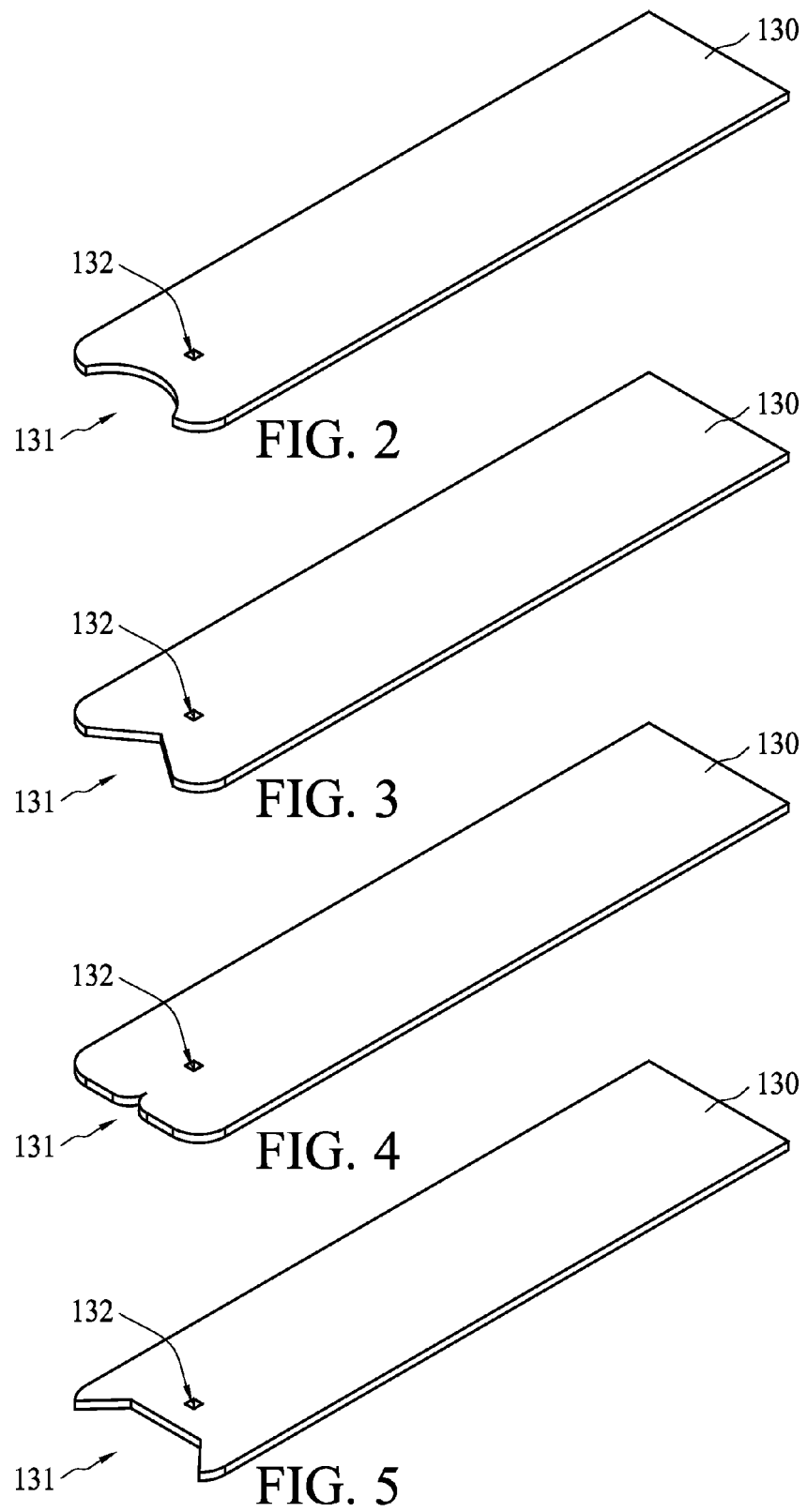

ELECTRODE STRIP AND SENSOR STRIP AND MANUFACTURE METHOD THEREOF AND SYSTEM THEREOF

The present application claims priority from Taiwanese application Ser. No. 101126157, filed on Jul. 20, 2012, of the same title and inventorship herewith.

The application is a divisional of U.S. patent application Ser. No. 13/725,244, filed Dec. 21, 2012.

BACKGROUND

1. Technical Field

The present disclosure relates to an electrode strip and a sensor strip, and more particularly, to an electrode strip and a sensor strip having two reactive areas. Notably, the sample liquids accommodated in one reactive area do not contaminate the sample liquids accommodated in the other reactive area.

2. Background

Electrodes made by utilizing electrochemical methods can be divided into two types: enzymatic electrodes and non-enzymatic electrodes. At the present time, the majority of electrodes mentioned in technical literature and used in biological substance measuring are enzymatic electrodes, such as well-commercialized blood sugar electrodes. In regard to non-enzymatic electrodes, most of them are used in the testing of general chemical compounds, such as pH electrodes for testing hydrogen ions. Since many enzymatic electrodes have restrictive conditions for moisture preservation, complicated manufacturing processes, and over-elaborate control conditions, manufacturing costs are quite high and mass production is not feasible, and thus, they are only suitable for use by technicians in research organizations and large scale medical testing units.

Relating to the prior art of non-enzymatic electrode strips, such as an electric current non-enzymatic electrode strip disclosed in U.S. Pat. No. 6,258,230 B1, the manufacturing process uses screen printing to spread the reaction layer formulation to cover two electrode systems. The composition of the reaction layer formulation requires large amounts of polymers mixed with a salt buffer. However, the analyte concentration, measured by the above-identified non-enzymatic electrode strips, is usually interfered by variant hematocrit factors in the blood samples.

The electrochemical method is one of the typical methods for measuring analyte concentration and involves amperometric responses indicative of the concentration of the analyte. An important limitation of electrochemical methods of measuring the concentration of the analyte in blood is the effect of confounding variables on the diffusion of analyte and the various active ingredients of the reagent. Moreover, the electrochemical method has a problem in that the accuracy of the analyte concentration is interfered by hematocrit concentrations (a ratio of the volume of packed red blood cells to the total blood volume).

The normal hematocrit range for an average human being is about 35% to 45%, though in extreme cases, the hematocrit may range from about 20% to about 70%. The mean hematocrit range for a neonatal infant is about 53% to 69%.

Variations in a volume of red blood cells within blood can cause variations in glucose readings measured by electrochemical sensor strips. Typically, a negative bias (i.e., lower calculated analyte concentration) is observed at high hematocrit levels, while a positive bias (i.e., higher calculated analyte concentration) is observed at low hematocrit levels. At high hematocrit levels, the red blood cells may impede the reaction of enzymes and electrochemical mediators, reduce the rate of chemistry dissolution, since there less plasma volume to solvate the chemical reactants, and slow diffusion of the mediator, causing a slower current result. Conversely, at low hematocrit levels, a higher measured current can result. In addition, the blood sample resistance is also hematocrit dependent, which can affect voltage and/or current measurements.

Additionally, the variation of hematocrit levels is extremely broad, and therefore, needs to be measured by a biosensor and biosensor strips. It is highly crucial to design biosensor strips and a biosensor which effectively prevent hematocrit from interfering. How to make a system and a method to prevent hematocrit from interfering with an analyte measurement is needed by the present related manufactory.

U.S. Pat. No. 7,407,811 ('811) described a method for measuring the analyte concentration. The method utilizes an alternative current (AC) excitation to measure hematocrit for correcting the analyte concentration and reducing hematocrit from interfering. Further, the method of '811 is the measuring phase angle and admittance magnitude of the AC excitation and cooperated with a formula to detect hematocrit. '811 further described the blood glucose measurement for correcting hematocrit by using the above hematocrit measurement method, which applies DC and AC signals in only one electrode set and only one reaction zone of a biosensor strip, whether applying AC or DC signal firstly. The phase angle and admittance magnitude of AC excitation is utilized to detect hematocrit, while DC excitation is utilized to detect analyte concentration. Furthermore, parameters of a set formula of the prior method further include temperature, and therefore, the analyte concentration will be corrected with the phase angle, admittance magnitude and temperature. Additionally, the provided AC excitation uses at least two frequencies and may use two to five frequencies in practice, and therefore, the hematocrit is detected by the applied AC excitation using different frequencies.

The method of '811 provides AC and DC signals to a sample in the same reaction zone and further uses only one electrode set for detection, and consequentially, there could be noise produced which would interfere with each other. In addition, a result of uncorrected analyte concentration and hematocrit measured by the provided AC with DC offset to the same reaction zone will interfere with each other's result and then influence the accuracy. The method of '811 further needs the appropriate temperature and two to five AC frequencies to correct the measured analyte concentration, which requires complex operations and an extended amount of time. Furthermore, the cost and complexity of the meter increases as the number of measurements and frequencies increase. Thus, an effective system and method are needed in order to solve the foregoing problem.

U.S. Pat. No. 5,264,103 ('103) describes a biosensor including two electrode sets which are disposed in two separated reactive areas, respectively. Two electrode sets are disposed on two sides of a single substrate. Although the substrate separates one electrode set from the other electrode set, two electrode sets might be easily interfered by each other due to adjacency between the upper electrode set and the lower electrode set. For instance, when the upper electrode set is applied with an AC signal for measuring hematocrit levels, a response signal in the lower electrode set will be induced in response to the AC signal of the upper electrode set due to the electrical coupling and as a result, the DC signal applied to the lower electrode will be interfered.

Thus, the design of '103 cannot perform a simultaneous measurement in the upper electrode of the first reactive area and the lower electrode of the second reactive area. In addition, the biosensor strip of '103 includes two vent holes disposed on two opposite sides of the substrate. However, if the amount of sample liquid exceeds the capacity of the biosensor strip, the sample liquids may overflow the vent hole and cause contamination. Furthermore, if two electrode sets are disposed on two opposite sides of the substrate, the substrate with a printed electrode set has to be upside down for printing the other electrode set on the substrate in the manufacturing process. Since the substrate with the two electrode sets is placed on a friction surface, the electrode set printed on the lower surface of the substrate is easily abraded in the manufacturing process.

In addition, many electrochemical biosensor strips sold on the market have another problem in that a sample volume will also influence the accuracy. In the measurement of blood glucose, for example, it is quite sensitive to blood sample volume, and if the sample is insufficient, then that will cause an error in the calculation. Thus, an effective system and method are needed in order to solve the above disadvantage.

SUMMARY

In order to improve the above-identified disadvantage, the present disclosure provides a sensor strip and an electrode strip for hematocrit correction. Both of which have two separated electrode sets in different reactive areas for measuring either hematocrit or the analyte concentration.

In accordance with the above-mentioned disadvantage, the present disclosure provides a sensor strip and an electrode strip having two independent reactive areas which do not contaminate each other so as to reduce the signals (such as the AC signal and the DC signal) interfering at the same electrode set in the same reactive area or to reduce the signals interfering at distinct electrode sets in separated reactive areas. Since the present disclosure does not require an appropriate temperature for correcting the analyte concentration, an electrode strip or a sensor strip having conditions for a strengthened structure of the present disclosure provides simple operations and low cost requirements.

The present disclosure further provides an electrode strip having two reactive areas. The electrode strip includes a first substrate, a first electrode set disposed on the first substrate, a first insulation layer, a second substrate, a second electrode set and a second insulation layer. The first insulation layer is disposed on the first electrode set and includes a first opening. The second substrate is disposed on the first insulation layer and includes a sampling opening and a connecting hole. The second electrode set is disposed on the second substrate and uncovers the connecting hole. The second insulation layer includes a second opening which is vertically connected with the first opening through the connecting hole.

The present disclosure provides a sensor strip having two reactive areas. The sensor strip comprises a first reactive film, a second reactive film and a vent hole. The first reactive film includes a substrate, a first electrode layer disposed on the substrate and a first insulation layer. The first insulation layer is disposed on the first electrode layer and includes a first end, which is concaved to form a first reactive area with a first depth. The second reactive film includes a second electrode layer disposed on the first insulation layer and a second insulation layer that is disposed on the second electrode layer and includes a first end. The first end of the second insulation layer is concaved to form a second reactive area with a second depth. Furthermore, the vent hole penetrates the second insulation layer, the second electrode layer and the first insulation layer to connect the first reactive area and the second reactive area.

The present disclosure also provides a manufacturing method of a sensor strip and the method includes the following steps: providing a first reactive film and a second reactive film, wherein the first reactive film includes a first reactive area and the second reactive film includes a second reactive area; disposing the first reactive film on the second reactive film; and forming a vent hole which penetrates the first reactive film and connects the first reactive area and the second reactive area.

Furthermore, the present disclosure also provides a manufacturing method of an electrode strip and the method includes the following steps: providing a first substrate; disposing a first electrode set on the first substrate; forming a first insulation layer on the first electrode set, wherein the first insulation layer includes a first opening; disposing a second substrate on the first insulation layer, wherein the second substrate includes a sampling opening and a connecting hole; disposing a second electrode set on the second substrate, wherein the second electrode set uncovers the connecting hole; and forming a second insulation layer on the second electrode set, wherein the second insulation layer includes a second opening, wherein the connecting hole vertically connects the first opening and the second opening.

Moreover, the present disclosure also provides a measurement system with hematocrit correction and the measurement system includes either the above-mentioned electrode strip or sensor strip and a sensor. Either the first electrode set of the electrode strip or the first electrode layer of the sensor strip is configured to measure an analyte concentration, while the second electrode set of the electrode strip or the second electrode layer of the sensor strip is configured for measuring hematocrit from the same sample. The sensor includes a power source, a detector and a microprocessor. The power source is configured to simultaneously provide a DC signal and an AC signal. The DC signal is transmitted to either the first electrode set or the first electrode layer while the AC signal is transmitted to either the second electrode set or the second electrode layer. The detector is configured to detect a first reactive value in response to the analyte concentration and a second reactive value in response to hematocrit concentration. The microprocessor is configured to calculate the hematocrit-corrected analyte concentration in response to the first reactive value and the second reactive value.

Another function of the present disclosure will be described in the following paragraphs. Certain functions can be realized in the present section, while the other functions can be realized in the detailed description. In addition, the indicated components and the assembly can be explained and achieved by the details of the present disclosure. Notably, the previous explanation and the following description are demonstrated and are not limited to the scope of the present disclosure.

The foregoing has outlined rather broadly the features and technical benefits of the disclosure in order that the detailed description of the disclosure that follows may be better understood. Additional features and benefits of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the disclosure. It should also be realized by those skilled in the art that such equivalent constructions do not depart from the spirit and scope of the disclosure as set forth in the appended claims.

BRIEF DESCRIPTION OF THE DRAWINGS

The accompanying drawings, which are incorporated in and constitute a part of this specification, illustrate embodiments of the disclosure and, together with the description, serve to explain the principles of the invention.

The foregoing summary, as well as the following detailed description of the invention, will be better understood when read in conjunction with the appended drawings. For the purpose of illustrating the invention, there are shown in the drawings examples which are presently preferred. It should be understood, however, that the invention is not limited to the precise arrangements and instrumentalities shown.

Figure 1:
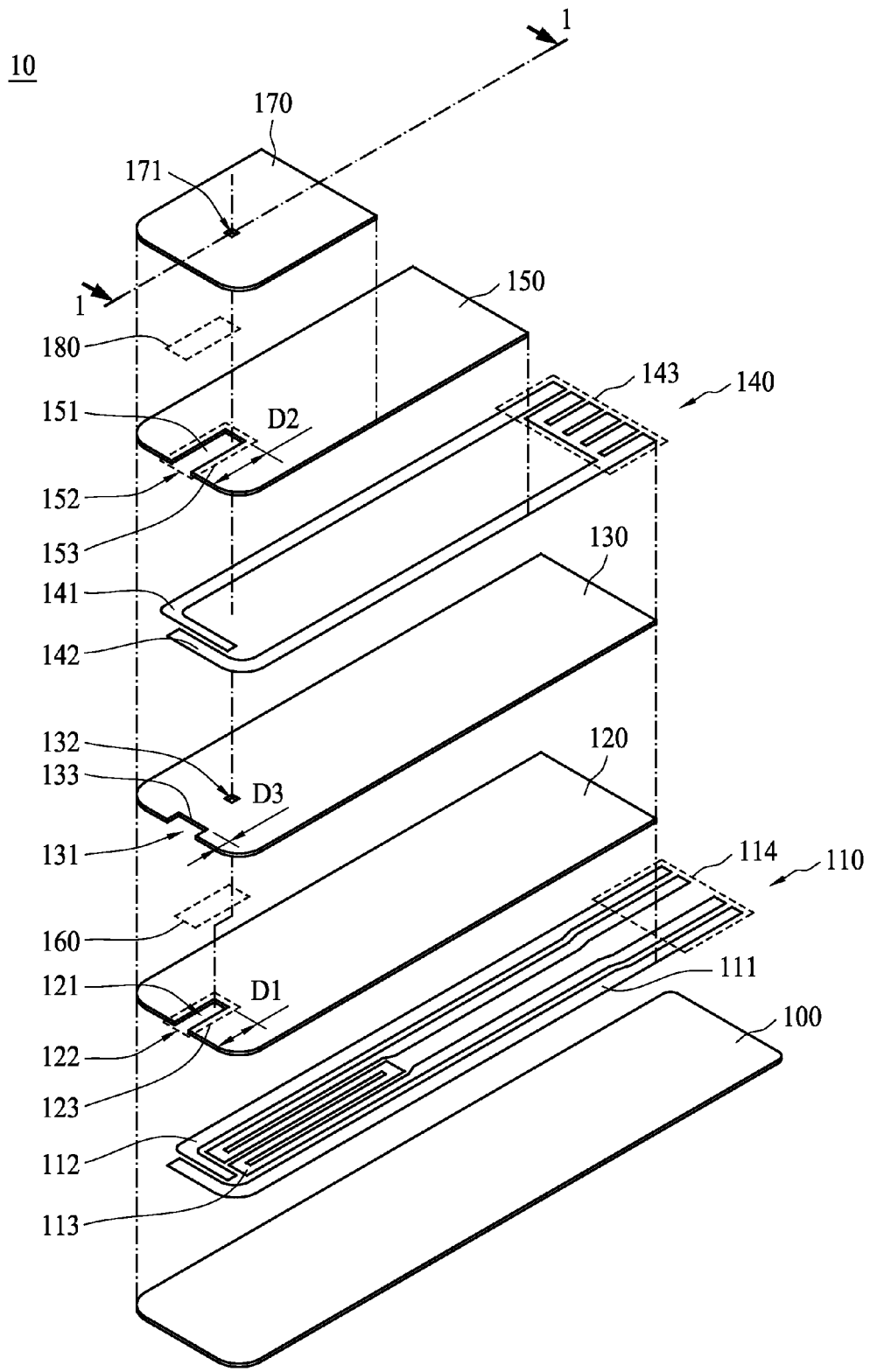
Figure 6:
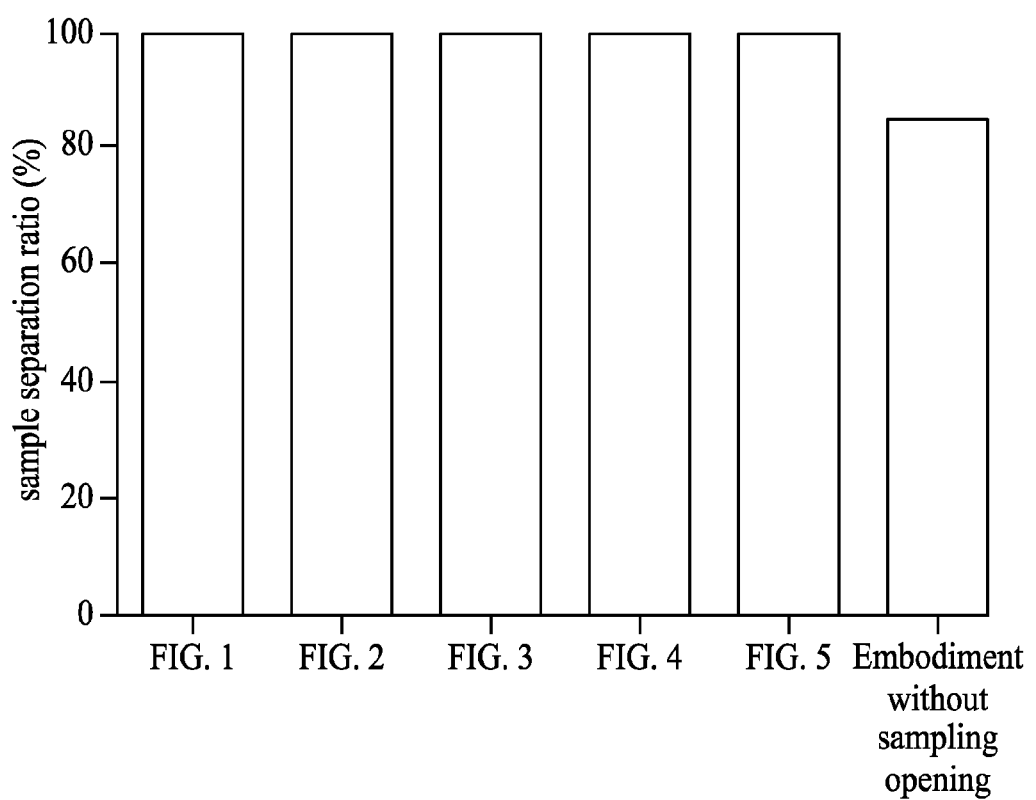
Figure 7:
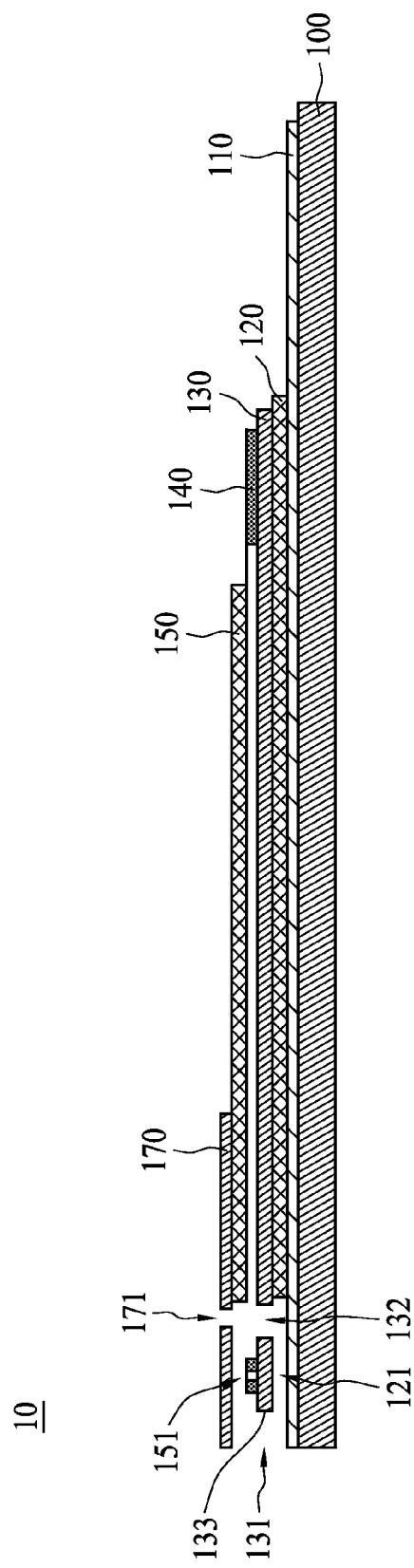
Figure 8:
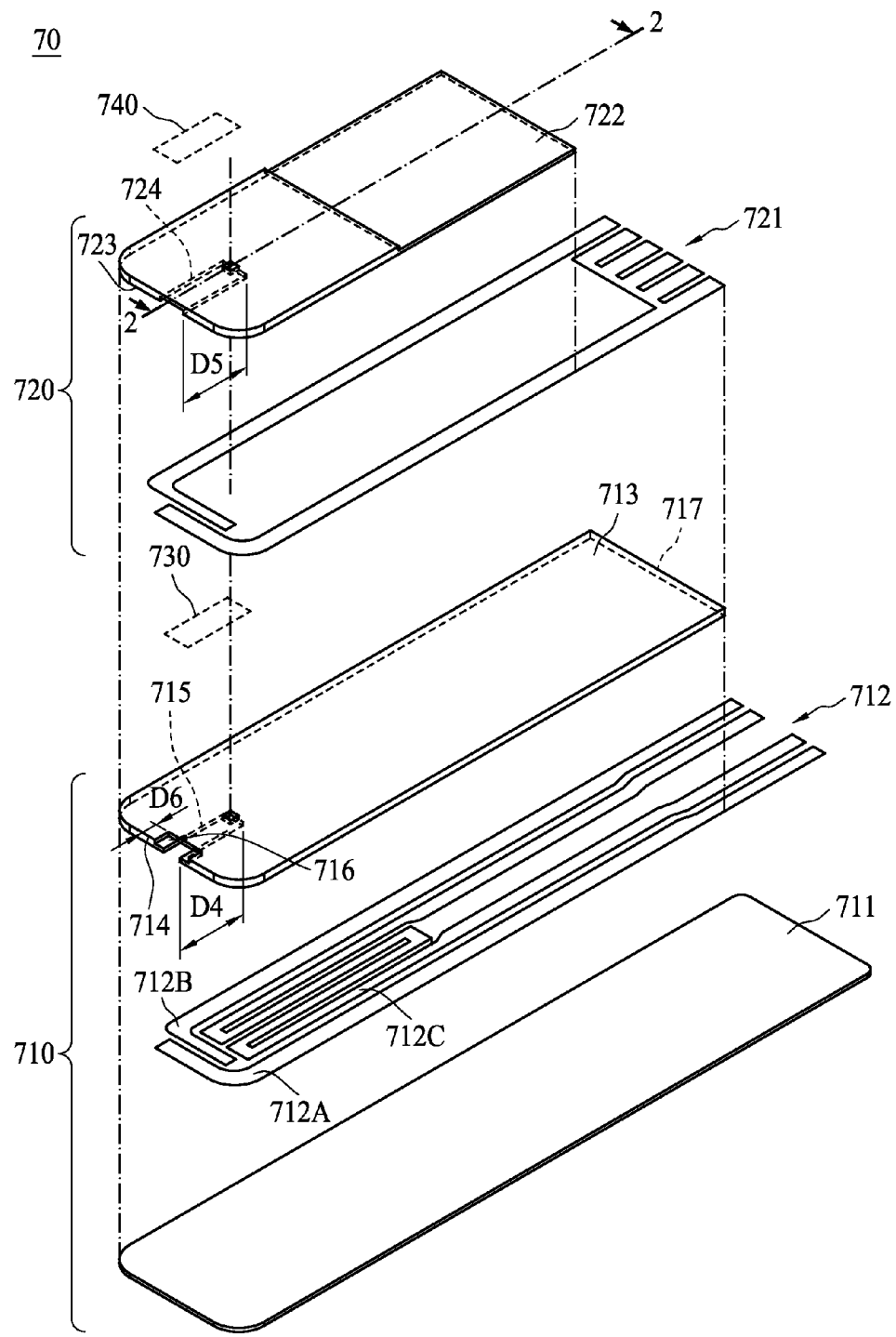
Figure 9:
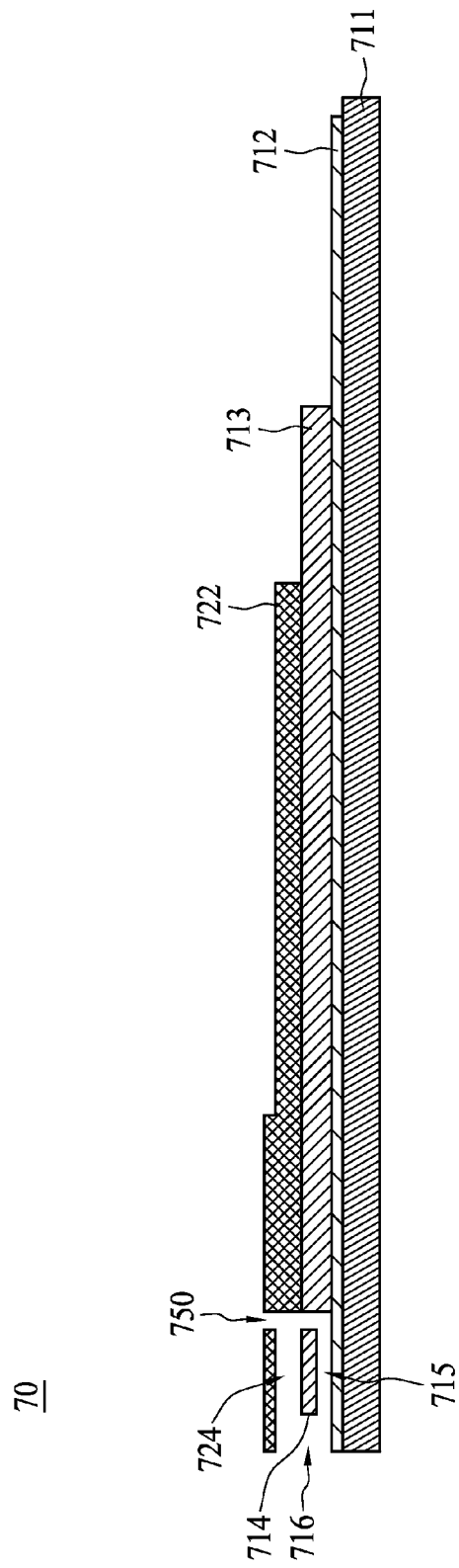
Figure 10:
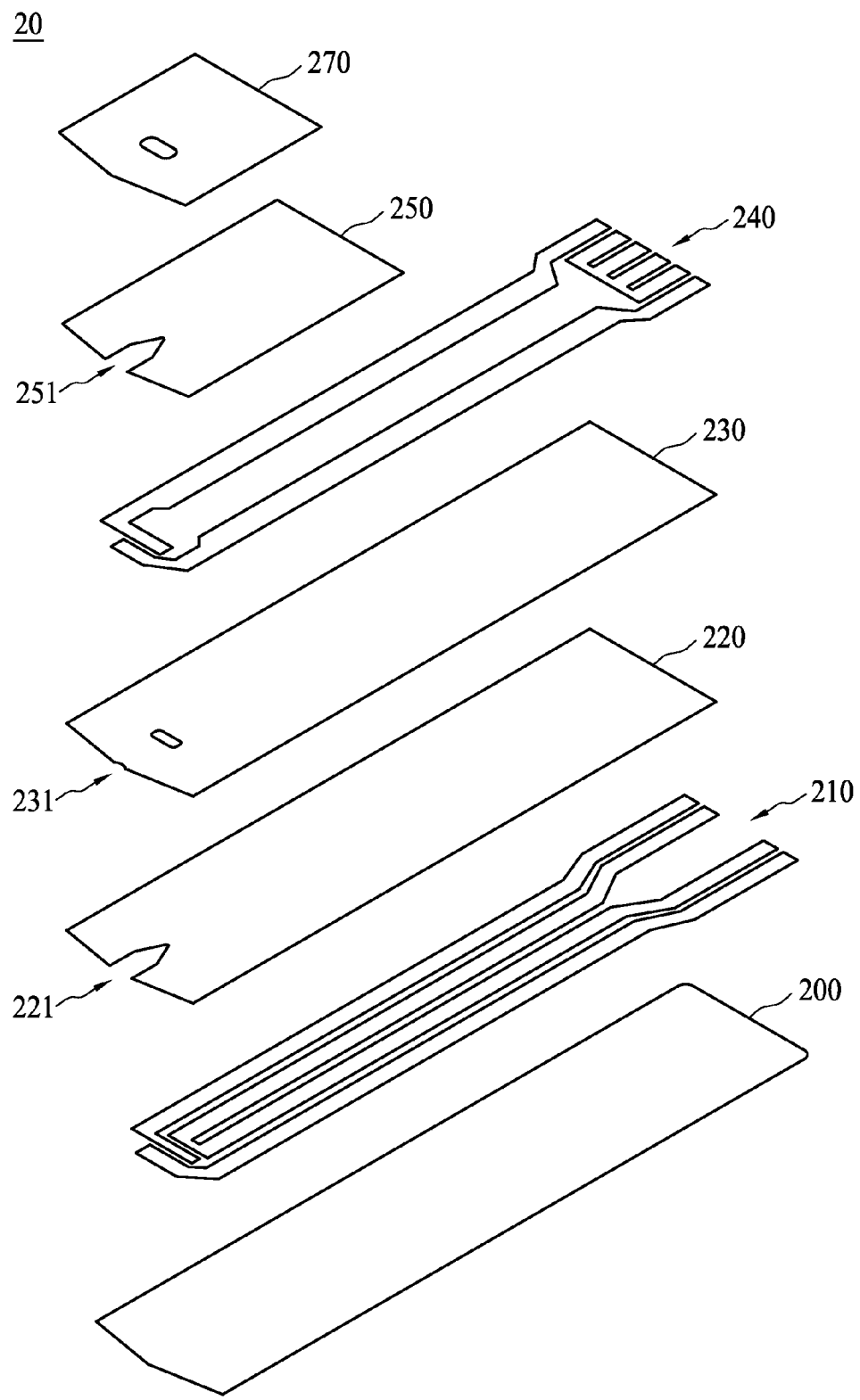
Figure 11:
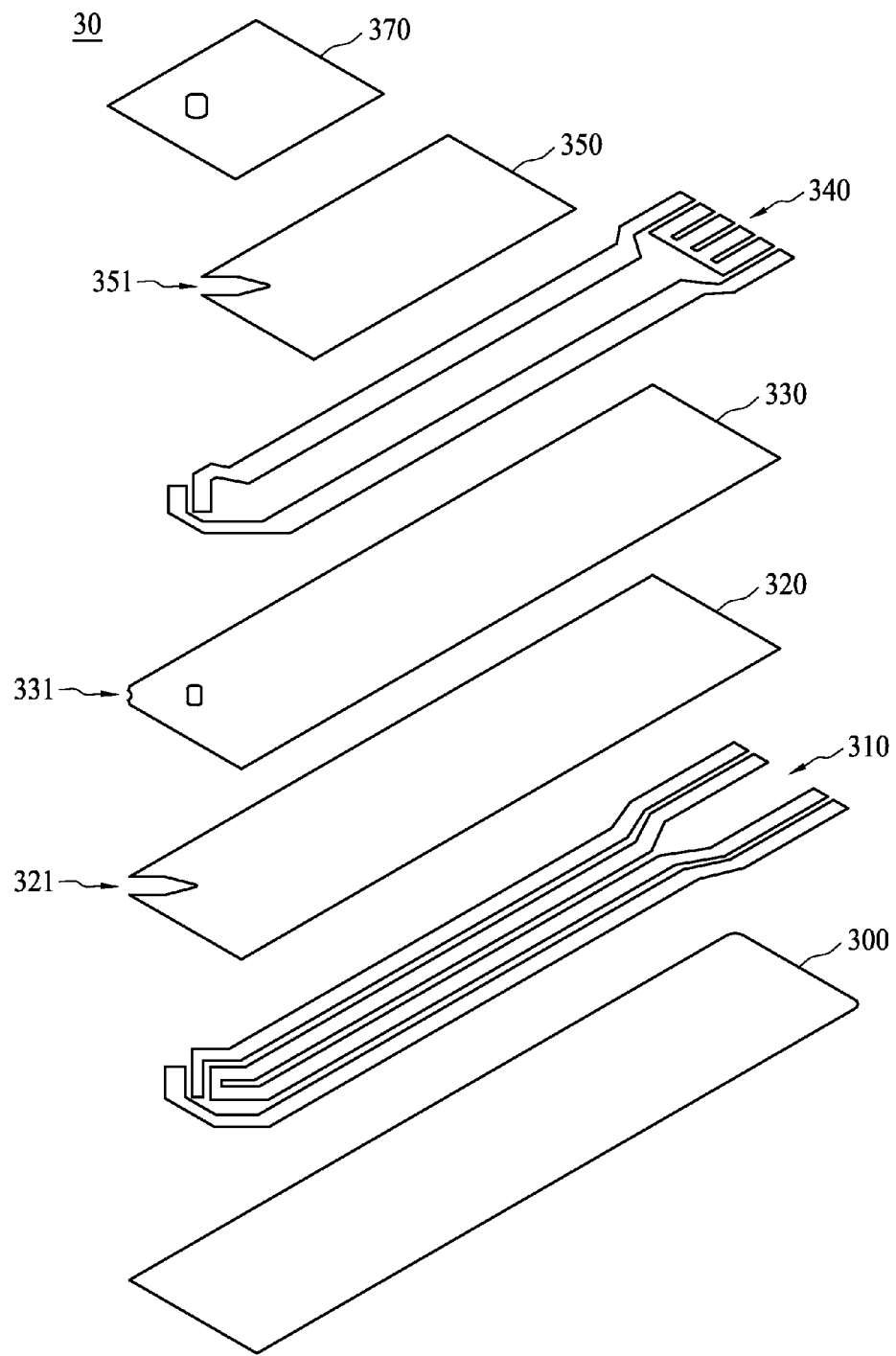
Figure 12:
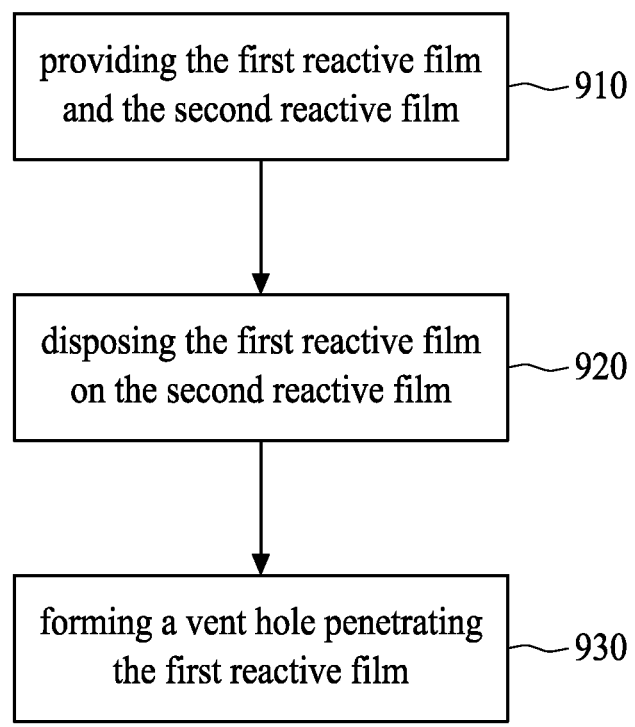
Figure 13:
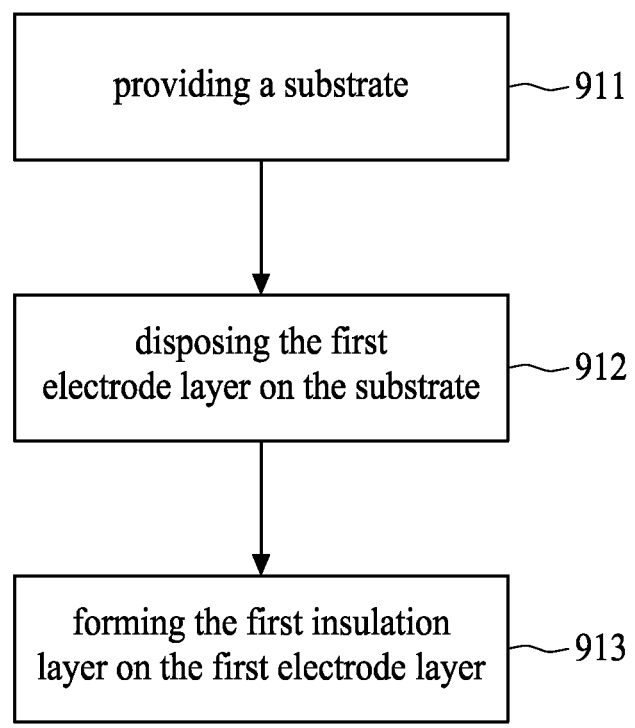
Figure 14:
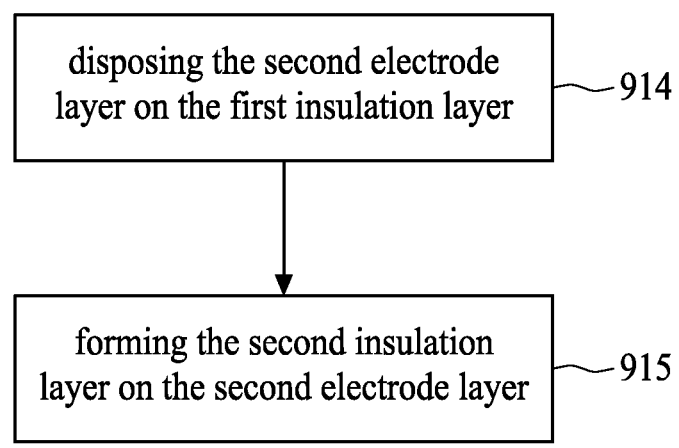
Figure 15:
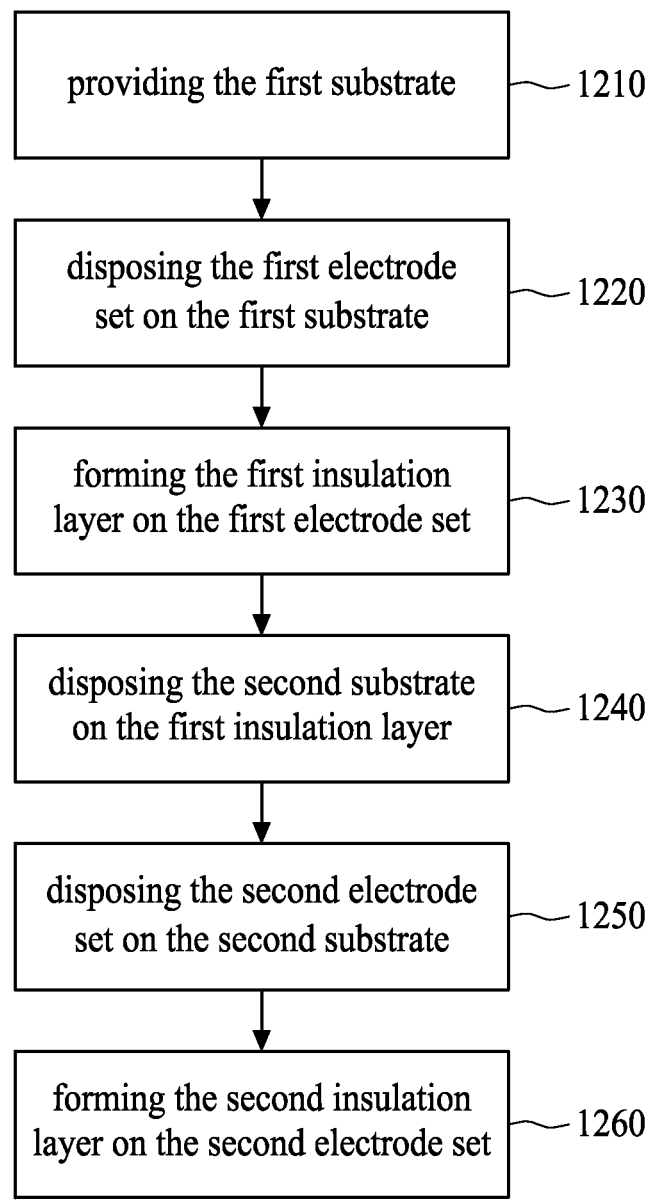

A more complete understanding of the present disclosure may be derived by referring to the detailed description and claims when considered in connection with the Figures, where like reference numbers refer to similar elements throughout the Figures, and:

FIG. 1 is a schematic view of an electrode strip in accordance with an embodiment of the present disclosure;

FIG. 2 is a schematic view of a sampling opening of the second substrate in accordance with a second embodiment of the present disclosure;

FIG. 3 is a schematic view of a sampling opening of the second substrate in accordance with a third embodiment of the present disclosure;

FIG. 4 is a schematic view of a sampling opening of the second substrate in accordance with a fourth embodiment of the present disclosure;

FIG. 5 is a schematic view of a sampling opening of the second substrate in accordance with a fifth embodiment of the present disclosure;

FIG. 6 is a bar chart of the sample separation ratio in accordance with embodiments shown in FIG. 1 to FIG. 5 of the present disclosure;

FIG. 7 is a cross-sectional view of the embodiment of FIG. 1 along with a cross-sectional line 1-1 in accordance with the embodiment of the present disclosure;

FIG. 8 is a schematic view of a sensor strip in accordance with another embodiment of the present disclosure;

FIG. 9 is a cross-sectional view of the embodiment of FIG. 7 along with a cross-sectional line 2-2 in accordance with the embodiment of the present disclosure;

FIG. 10 illustrates a schematic view of another electrode strip in accordance with another embodiment of the present disclosure;

FIG. 11 illustrates a schematic view of another electrode strip in accordance with another embodiment of the present disclosure;

FIG. 12 illustrates a flow chart of a manufacturing method of a sensor strip in accordance with another embodiment of the present disclosure;

FIG. 13 illustrates a flow chart of a step of providing the first reactive film in accordance with the embodiment in FIG. 12 of the present disclosure;

FIG. 14 illustrates a flow chart of a step of providing the second reactive film in accordance with another embodiment in FIG. 12 of the present disclosure; and FIG. 15 illustrates a flow chart of a manufacturing method of the electrode strip in accordance with another embodiment of the present disclosure.

DETAILED DESCRIPTION

The present disclosure is directed to an electrode strip, a sensor strip, a manufacturing method thereof and a measurement system thereof. In order to make the present disclosure completely comprehensible, detailed steps and structures are provided in the following description. Obviously, implementation of the present disclosure does not limit special details known by persons skilled in the art. In addition, known structures and steps are not described in details, so as not to limit the present disclosure unnecessarily. Preferred embodiments of the present disclosure will be described below in detail. However, in addition to the detailed description, the present disclosure may also be widely implemented in other embodiments. The scope of the present disclosure is not limited to the detailed embodiments, and is defined by the claims.

The following description of the disclosure accompanies drawings, which are incorporated in and constitute a part of this specification, and illustrate embodiments of the disclosure, but the disclosure is not limited to the embodiments. In addition, the following embodiments can be properly integrated to complete another embodiment.

References to "one embodiment," "an embodiment," "other embodiments," "another embodiment," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, although it may.

Unless specifically stated otherwise, as apparent from the following discussions, it is appreciated that throughout the specification discussions utilizing terms such as "measuring," "receiving," "calculating," "detecting," "transmitting," or the like, refer to the action and/or processes of a computer or computing system, or similar electronic computing device, state machine and the like that manipulate and/or transform data represented as physical, such as electronic, quantities into other data similarly represented as physical quantities.

In addition, unless specifically stated otherwise, as apparent from claims and detailed description, it is appreciated that throughout the specification the quantity of components is single. If the quantity of the labeled component is one, the quantifier is explained to include one unit or at least one unit. If the quantity of the labeled component is a plurality, the quantifier is explained to include at least two units.

The present disclosure relates to an electrode strip and a sensor strip having two independent reactive areas. When a major reactive area performs its electrochemical reaction, the other minor reactive area is capable of measuring a factor which allows correcting of the analyte concentration detected in the major reactive area so as to obtain a higher accuracy of analyte concentration in the electrode strips and sensor strips.

In accordance with an embodiment of the present disclosure, when the major reactive area is configured to measure blood sugar, the minor reactive area is configured to detect an interfering factor for correcting the readings of blood sugar. The interfering factor is selected, but not limited, from hematocrit, triglyceride, cholesterol, uric acid, maltose, galactose, ascorbic acid, acetaminophenol, L-3,4-dihydroxyphenylalanine and dopamine.

In accordance with another embodiment of the present disclosure, when the major reactive area is configured to measure cholesterol, the minor reactive area is configured to detect an interfering factor for correcting the readings of cholesterol. Such an interfering factor is selected, but not limited, from hematocrit, hemoglobin, ascorbic acid, and methyl-3,4-dihydroxyphenylalanine.

In accordance with another embodiment of the present disclosure, when the major reactive area is configured to measure uric acid, the minor reactive area is configured to detect an interfering factor for correcting the readings of uric acid. Such an interfering factor is selected, but not limited, from hematocrit, hemoglobin, bilirubin and methyl-3,4-dihydroxyphenylalanine.

In accordance with another embodiment of the present disclosure, when the major reactive area is configured to measure hemoglobin, the minor reactive area is configured to detect an interfering factor for correcting the readings of hemoglobin. Such an interfering factor is selected, but not limited, from hematocrit.

In accordance with another embodiment of the present disclosure, when the major reactive area is configured to measure lactic acid, the minor reactive area is configured to detect an interfering factor for correcting the readings of lactic acid. Such an interfering factor is selected, but not limited, from hematocrit, ascorbic acid, acetaminophenol and dopamine.

The so-called "substrate" in the present disclosure refers to a thin-layered plate with a flat surface and electric insulating properties. More preferably, the insulating substrate is selected, but not limited, from the group consisting of polyvinyl chloride (PVC) plates, fiber glass (FR-4) plates, polyester sulphone, bakelite plates, polyester (PET) plates, polycarbonate (PC) plates, glass plates and ceramic plates (CEM-1). Particularly, the thickness of the substrate ranges from 0.03 mm to 0.7 mm, from 0.07 mm to 0.15 mm, or from 0.5 mm to 0.62 mm.

The so-called "electrode set" or "electrode layer" in the present disclosure includes at least two metal electrodes that are isolated and disconnected from each other and used to connect the electric current biosensor. According to the preferred embodiment of the present disclosure, either the electrode set or the electrode layer is partly covered by an electric insulating layer. An end of both metal electrodes is exposed by the electric insulation layer, which include a working electrode and a reference electrode, and the other end of which forms connections of the working electrode and the reference electrode. The connections are used to connect the sensor, while the electric effect is evoked during the electrochemical reaction caused by the analyte and the aforementioned sensor. More preferably, the components used in the electrode layer or the electrode set can include carbon paste, gold paste, silver paste, mixed carbon-silver paste, evaporated graphite or copper paste, or a combination thereof (e.g., screen printing of silver paste initially, followed by printing of carbon paste), or any conductive paste material that is suitable for screen printing and can be dried at below 80° C.

The so-called "insulation layer" in the present disclosure refers to a thin layer formed by a material with electric insulating properties and partially covering the electrode set or the electrode layer. According to a preferable embodiment of the present disclosure, the electric insulation layer does not cover the reaction zone and the connections of the electrode set or the electrode layer, and is formed on the substrate. Accordingly, the material of the insulation layer is selected, but not limited, from PVC insulation tape, PET insulation tape, thermal curing adhesive and ultraviolet photo-curable adhesive. More preferably, the insulation layer has a thickness of 0.01 to 0.6 mm, 0.4 to 0.51 mm, or 0.02 to 0.03 mm.

The so-called "reaction layer formulation" in the present disclosure includes an electron mediator and a surfactant. In another embodiment, the reaction layer formulation further includes specific enzymes or water-soluble polymer carriers.

The "electron mediator" disclosed in the present application refers to a substance that, after reacting with the analyte to be tested in the whole blood sample (such as uric acid or hemoglobin), can itself be reduced from the oxidized state to the reduced state. When the electron mediator is changed into the reduced state, an external potential can be applied to the electrode strip to prompt the electron mediator to return to the oxidized state from the reduced state. At this time, the variations of potential, resistance or current due to the chemical reaction can be transmitted to connections at the other ends of the electrode set or the electrode layer by the working electrode and the reference electrode by contact with the conductive film and the reaction layer. When the whole blood detecting electrode strip is connected to a biosensor, the biosensor can apply an external potential to the electrode strip, through a potential output device or power source, to receive the aforementioned change of potential, resistance or current due to the chemical reaction through a signal receiver or detector, and convert the signal into the concentration of the target compound through a display device. According to a preferred embodiment of the present disclosure, the electron mediator can be potassium ferricyanide. More preferably, the amount of the electron mediator ranges from 0.05% to 6% of the reaction layer formulation (calculated by weight). Even more preferably, when using the whole blood detecting electrode strip for the detection of uric acid, the amount of the electron mediator ranges about 0.3% of the reaction layer formulation (calculated by weight), and when using the whole blood detecting electrode strip for the detection of hemoglobin, the amount of the electron mediator ranges about 3% of the reaction layer formulation (calculated by weight).

The so-called "surfactant" in the present disclosure refers to a substance for increasing the reaction between a test sample and the electron mediator. The surfactant is selected from, but is not limited to, Sodium dodecyl sulfate, Sodium dodecyl sulfonate, Tween 20, Triton X-100, Sodium cholate and the derivatives thereof. The amount of the surfactant ranges about 0.01% to 1% of the reaction layer formulation (calculated by weight).

The so-called "water-soluble polymer carrier" in the present disclosure refers to a substance that makes the electron mediator, once dried, adhere to the electric insulating substrate and strengthens the contact between the reaction layer and the liquid sample. More preferably, the molecular diameter of the water-soluble polymer carrier is smaller than 100 microns, thereby enabling the water-soluble polymer carrier to be dispersed evenly in the reaction film formulation solution and will not easily precipitate. After the reaction layer has been dried, if the distribution of the water-soluble polymer carrier is uneven, it will cause poor conductivity or will function unevenly between the water-soluble electron mediator and the liquid sample, resulting in an inaccurate test result. More preferably, the water-soluble polymer carrier can be selected from the group consisting of polyvinyl acetate (PVA), polyvinyl pyrrolidone (PVP), polyethylene glycol (PEG), gelatin, carboxymethyl cellulose (CMC), methyl cellulose, and the mixture thereof. More preferably, the amount of the water-soluble polymer carrier is below 5% of the reaction layer formulation (calculated by weight).

FIG. 1 illustrates a schematic view of an electrode strip 10 in accordance with an embodiment of the present disclosure. The electrode strip 10 includes a first substrate 100, a first electrode set 110, a first insulation layer 120, a second substrate 130, a second electrode set 140 and a second insulation layer 150.

In the embodiment shown in FIG. 1, the material of the first substrate 100 may be a PVC plate. The first electrode set 110 is disposed on the first substrate 100. The first electrode set 110 includes a reference electrode 111, a working electrode 112 and a sensing electrode 113. Since the location of the sensing electrode 113, corresponding to locations of the reference electrode 111 and working electrode 112, is far from the opening 122 of the first insulation layer 120, the sensing electrode 113 can ensure that the reference electrode 111 and the working electrode 112 have reacted to the blood sample, which finally reaches the sensing electrode 113. In other embodiments (not shown), the electrode strip 10 may further include a plurality of multifunctional electrodes for confirming whether the electrode strip is received inside the above-mentioned sensor (not shown).

In the embodiment shown in FIG. 1, the first insulation layer 120 is disposed on the first electrode set 110 and includes a first opening 121, which exposes the reference electrode 111, the working electrode 112 and sensing electrode 113 of the first electrode set 110. In addition, the first insulation layer 120 also uncovers the connection 114, which is far from the first opening 121. The connection 114 is configured to electrically connect with the sensor (not shown). In other words, the first insulation layer 120 does not cover the connection 114 of the first electrode set 110.

When the second substrate 130 is disposed on the first insulation layer 120, the first opening 121 is located between the first substrate 100 and the second substrate 130 to form a first reactive area 123 (indicated with dotted line). In the embodiment shown in FIG. 1, the second substrate 130 includes a sampling opening 131 and a connecting hole 132. The sampling opening 131 is capable of removing the surface tension of the sample liquid so as to smoothly conduct the sample liquid into the first reactive area 123. Furthermore, the connecting hole 132 is configured to construct a capillary attraction to guide the sample liquid into the first reactive area 123.

In the embodiment shown in FIG. 1, the electrode strip 10 further includes a first reaction layer 160 (indicated with dotted line), which is a film covering on the first reactive area 123. The reaction layer formulation is added dropwise or printed onto the first reactive area 123 to form a first reaction layer 160.

The second electrode set 140 is disposed on the second substrate 130. Notably, the reference electrode 141 and the working electrode 142 of the second electrode set 140 uncover the connecting hole 132 of the second substrate 130. In other words, the gaseous molecules of the connecting hole 132 may diffuse into the second electrode set 140. In the embodiment, an AC signal or an AC with DC offset signal may be applied to the second electrode set 140 for measuring hematocrit levels or the above-mentioned interfering factors from the minor reactive area. In other words, the first electrode set 110 is applied by a DC signal for measuring the above-identified test samples in the major reactive area. Moreover, since the first electrode set 110 and the second electrode set 140 are disposed on different substrates, when the first electrode 110 measures the hematocrit, the signal of the first electrode set 110 does not interfere with the DC signal applied to the second electrode set 140. Furthermore, since the first electrode set 110 and the second electrode set 140 are not disposed on two opposite sides of a single substrate, the first electrode set 110 or the second electrode set 140 can avoid abrasion in the manufacturing process.

As shown in FIG. 1, the second insulation layer 150 includes a second opening 151, which has an aperture 152. In the embodiment, the electrode strip 10 further includes a cover 170, which is disposed on the second insulation layer 150 and includes a through hole 171. In addition, the second opening 151 is located between the cover 170 and the second substrate 130 to form a second reactive area 153 (indicated with dotted lines). In the embodiment, the electrode strip 10 further includes a second reaction layer 180 (indicated with dotted lines), which is a film that covers the second reactive area 153. The reaction layer formulation is added dropwise or printed onto the second reactive area 153 so as to form a second reaction layer 180.

Furthermore, the second insulation layer 150 also uncovers the connection 143 of the second electrode set 140 which is far from the second opening 151. The connection 143 is configured to electrically connect with a sensor (not shown). In other words, the second insulation layer 150 exposes the connection 143 of the second electrode set 140. Moreover, the connection 114 of the first electrode set 110 does not overlap with the connection 143 of the second electrode set 140.

As shown in FIG. 1, the connecting hole 132 vertically connects the first opening 121 and the second opening 151. Since the through hole 171 connects with the connecting hole 132 through the second opening 151, the gaseous molecules of the first opening 121 may diffuse out of the cover 170 through the connecting hole 132 and the through hole 171. In other words, when sample liquid is conducted into the first reactive area 123 and the second reactive area 153 through the sampling opening 131, the capillary attraction generated from the connecting hole 132 and the through hole 171 guides the sample liquid into the first reactive area 123 and the second reactive area 153. In the embodiment, the shape of the through hole 171 and the connecting hole 132 can be selected from a cylinder, a square pillar and a multilateral pillar, but both the through hole 171 and the connecting hole 132 do not necessarily have to be the same shape. Particularly, the inside diameter of the through hole 171 ranges from 1.6×0.7 mm to 2.0×1.1 mm, while the inside diameter of the connecting hole 132 ranges from 0.5×0.5 mm to 1.6×0.7 mm.

In order to conduct the sample liquid into the first reactive area 123 and the second reactive area 153 and to avoid cross-contamination between the sample liquid accommodated in the first reactive area 123 and the sample liquid in the second reactive area 153, the inside diameter of the connecting hole 132 can be designed to be smaller than or equal to the inside diameter of the through hole 151 to enhance capillary attraction and to avoid the sample liquid of the first reactive area 123 to contaminate the sample liquid of the second reactive area 153 through the connecting hole 132 and vice versa.

Furthermore, the first reactive area 123 of the present disclosure has a first depth D1, the second reactive area 153 has a second depth D2, and the sampling opening 131 has a third depth D3. In the embodiment, both, the first depth D1 and the second depth D2 are longer than the third depth D3. Since the first reactive area 123 and the second reactive area 153 accommodate sample liquids from the same source, the first depth D1 and the second depth D2 are configured to separate the sample liquid of the first reactive area 123 from the sample liquid of the second reactive area 153. Particularly, because the amount of the sample liquids entering the sampling opening 131 is constant, the capacity of the first reactive area 123 and the second reactive area 153 can be designed to accommodate half of the amount of the sample liquids, respectively. Thus, the sample liquids of the first reactive area 123 do not contaminate the sample liquids of the second reactive area 153. Additionally, in another embodiment (not shown), the first depth D1 of the first reactive area 123 may be longer than the second depth D2 of the second reactive area 153 and vice versa.

Moreover, the second substrate 130 of the present disclosure has an end 133 adjacent to the sampling opening 131. The end 133 where the sampling opening 131 is formed is a hydrophobic surface which is configured to separate sample liquids from the sampling opening 131 and to avoid sample liquid from staying in the sampling opening 131 and to avoid the sample liquids of the first reactive area 123 from contaminating the sample liquids of the second reactive area 153. As shown in FIG. 1, the third depth D3 of the sampling opening 131 is smaller than either the first depth D1 or the second depth D2. The third depth D3 may be 0.15 to 1.5 mm, or 0.3 to 0.8 mm.

In the embodiment shown in FIG. 1, both of the inside diameter of the aperture 122 of the first opening 121 and the inside diameter of the aperture 152 of the second opening 151 are smaller than the inside diameter of the sampling opening 131. In another embodiment (not shown), the inside diameter of either the aperture 122 or the aperture 152 can be designed to equal to the inside diameter of the sampling opening 131. In another embodiment (not shown), the inside diameter of either the aperture 122 or the aperture 152 may be designed to be larger than the inside diameter of the sampling opening 131. Since the sampling opening 131 is configured to remove the surface tension of the sample liquids, the shape of the sampling opening 131 of the second substrate 131 may be selected from semicircular (illustrated in FIG. 2), cuneal (illustrated in FIG. 3), water-drop (illustrated in FIG. 4) and concave (illustrated in FIG. 5). The sample liquids are separated by the sampling opening 131 and conducted into the first reactive area 123 and the second reactive area 153. In other words, the sampling opening 131 is capable of dividing the sample liquids into two parts. In addition, an experiment is performed to calculate sample separation ratios of the embodiments of FIG. 1 to FIG. 5 and the embodiment without any sampling opening. The experiment utilizes the same sample liquid and has a sampling count (e.g., 100 strips) for each group. As shown in FIG. 6, 15% of the electrode strip, without any sampling opening, cannot divide the sample liquids. In contrast, the other electrode strips are capable of separating the sample liquids of the first reactive area 123 from the other of the second reactive area 153.

FIG. 7 is a cross-sectional view of the cross-sectional line 1-1 of each of the layers of the electrode strip 10 shown in FIG. 1, once stacked up. The electrode strip 10 includes the first substrate 100, the first electrode set 110, the first insulation layer 120, the second substrate 130, the second electrode set 140, the second insulation layer 150 and a cover 170. In the embodiment shown in FIG. 7, since the through hole 171 of the cover 170 connects with the connecting hole 132 of the first insulation layer 120 through the second opening 151 and the second electrode set 140, the first opening 121 and the second opening 151 connect with each other. Because the end 133 of the sampling opening 121 is a hydrophobic surface, the sample liquids do not stay at the sampling opening 131 after the sample liquids enters into the sampling opening 131. Moreover, since capillary attraction of the first opening 121 and the second opening 151 will take in the sample liquids, the sample liquids do not stay at the sampling opening 131. Since the through hole 171 connects to the connecting hole 132, the gaseous molecules in the first opening 121 and the second opening 151, through the through hole 171, can be ejected. Moreover, compared with the patent of '103, the design of the upward through hole 171 in the cover 170 of the present disclosure can prevent the sample liquid from overflowing, which would result in contamination.

In the embodiment shown in FIG. 8, the present disclosure also provide a sensor strip 70, which comprises a first reactive film 710 and a second reactive film 720. The first reactive film 710 includes a substrate 711, a first electrode layer 712 and a first insulation layer 713. The first electrode layer 712 includes a reference electrode 712A, a working electrode 712B and a sensor electrode 712C. The first electrode layer 712 is disposed on the substrate 711 and is partially covered by the first insulation layer 713. In other words, the first electrode layer 712 is disposed between the first insulation layer 713 and the substrate 711. In the embodiment, the first insulation layer 713 includes a first end 714. The first end 714 adjacent to the first electrode layer 712 is concaved to form a first reactive area 715 that has a first depth D4. In addition, the first insulation layer 713 further includes a second end 717. The electrodes 712A, 712B, 712C of the first electrode layer 712 to which the second end 717 is adjacent are exposed by the first insulation layer 713.

As shown in FIG. 8, the second reactive film 720 includes a second electrode layer 721 and a second insulation layer 722. The second electrode layer 721 is disposed on the first insulation layer 713, while the second insulation layer 722 partially covers the second electrode layer 721. In other words, the second electrode layer 721 is disposed between the second insulation layer 722 and the first insulation layer 713. In the embodiment, the second insulation layer 722 includes a first end 723, which forms a concaved second reactive area 724 that has a second depth D5. In addition, the first insulation layer 713 has a first end 714. The first end 714 from which the substrate 711 is formed by a concaved sampling opening 716 that has a third depth D6. In other words, the first end 714 adjacent to the second electrode layer 721 forms the concaved sampling opening 716. In the embodiment, both, the first depth D4 and the second depth D5 are longer than the third depth D6. Furthermore, the second electrode layer 721 may be applied with an AC signal or an AC with DC offset signal for measuring hematocrit level or the above-identified interfering factors in the minor reactive areas. Thus, the first electrode layer 712 may be applied with a DC signal for measuring the aforesaid analyte in the major reactive area. However, in another embodiment (not shown), the first electrode layer 712 may be applied with the AC signal or the AC with DC offset signal for measuring hematocrit level or the above-identified interfering factors in the minor reactive areas. Therefore, the second electrode layer 721 may be applied with a DC signal for measuring the foregoing analyte in the major reactive area.

Moreover, the sensor strip 70 further includes a first reaction layer 730 and a second reaction layer 740. The first reaction layer 730 has a similar function and location with the first reaction layer 160, shown in FIG. 1. Similarly, the second reaction layer 740 and the second reaction layer 180 have similar functions and locations.

FIG. 9 is a cross-sectional view of the cross-sectional line 2-2 of each of the layers of the sensor strip 70 shown in FIG.

8, once stacked up. The sensor strip 70 includes a substrate 711, a first electrode layer 712, a first insulation layer 713, a second electrode layer 721 (referring to FIG. 8 and not shown in FIG. 9) and a second insulation layer 722. In the embodiment, the sensor strip 70 further includes a vent hole 750 which penetrates the second insulation layer 722, the second electrode layer 721 and the first insulation layer 713 so as to connect the first reactive area 715 and the second reactive area 724. When the sample liquid enters the first reactive area 715 and the second reactive area 724, respectively, the vent hole 750 is configured to eject the gaseous molecules and to generate capillary attraction. In the embodiment, the vent hole 750 is fabricated on the second insulation layer 722 and the first insulation layer 713 by a punch press method or a laser ablation method. The first reactive area 715 and the second reactive area 724 are capable of accommodating a sample liquid from the same source and since the first depth D4 of the first reactive area 715 and the second depth D5 of the second reactive area 724 are configured to separate the sample liquids of the first reactive area 715 from the sample liquids of the second reactive area 724, the sample liquids of the first reactive area 715 do not contaminate the sample liquid of the second reactive area 724. Furthermore, because the first end, which is far from the substrate 711, is a hydrophobic surface, the sample liquids, entering the first reactive area 715 and the second reactive area 724 from the sampling opening 716, do not stay at the hydrophobic surface (such as silicone surface) of the sampling opening 716 so as to avoid contamination between the sample liquids of the first reactive area 715 and the sample liquids of the second reactive area 724.

FIG. 10 illustrates another embodiment of the present disclosure. The electrode strip 20 of the embodiment includes a first substrate 200, a first electrode set 210, a first insulation layer 220, a second substrate 230, a second electrode set 240, a second insulation layer 250 and a cover 270. The structure and assembly of the electrode strip 20 and its components are similar with that of the electrode strip 10 shown in FIG. 1. The feature of the electrode strip 20 is that the cover 270, the second insulation layer 250, the second substrate 230, the first insulation layer 220 and the first substrate 200 include an awl-like shaped end. The sampling opening 231 is located at a tip area of the awl-like shaped end. In another embodiment (not shown), only the second substrate 230 of the electrode strip includes an awl-like shaped end. Because the awl-like shaped end converges toward the sampling opening 231 to reduce the contact area of the sampling opening 231, the amount of the sample liquids is drawn through the sampling opening 231 to the first opening 221 and the second opening 251 and decreases so as to prevent the sample liquids of the first opening 221 from contaminating the sample liquids of the second opening 251. Additionally, the above-mentioned design for reducing the contact area can be replaced with other designs that truncate the second substrate 230, where the sampling opening 231 is located, to reduce the contact area surrounding the sampling opening 231.

Additionally, in the embodiment shown in FIG. 10, the first insulation layer 220 and the second substrate 230 can be integrated as the first insulation layer 713 shown in FIG. 8. The second insulation layer 250 and the cover 270 can be integrated as the second insulation layer 722 shown in FIG. 8.

The embodiment shown in FIG. 11 is modified from the embodiment shown in FIG. 10. In the embodiment shown in FIG. 11, the electrode strip 30 includes a first substrate 300, a first electrode set 310, a first insulation layer 320, a second substrate 330, a second electrode set 340, a second insulation layer 350 and a cover 370. The structure and assembly of the electrode strip 30 is similar with that of the electrode strip 10 shown in FIG. 1. The feature of the electrode strip 30 is that the sampling opening 331 is disposed at the corner of the second substrate 330. Since the sampling opening 331 is located at the corner, the contact area of the sampling opening 331 will reduce so that the amount of sample liquids, through the sampling opening, entering the first opening 321 and the second opening 351 will reduce to avoid cross-contamination between the first opening 321 and the second opening 351. The difference between the embodiment of FIG. 11 and that of FIG. 10 is the locations of the sampling opening 231 and 331. In addition, as shown in FIG. 11, the first opening 321 and the second opening 351 may be disposed corresponding to the sampling opening 231. In the embodiment, the lengthwise axis of the first opening 321 and the lengthwise axis of the first insulation layer 330 intersect to form an included angle which ranges from 20° to 70°. Furthermore, the lengthwise axis of the second opening 351 and the lengthwise axis of the second insulation layer 350 intersect to form an included angle which also ranges from 20° to 70°. Similarly, the first electrode set 310 and the second electrode set 340 may bend toward the corner in response to the location of the sampling opening 331.

The flow chart shown in FIG. 12 illustrates a manufacturing method of the sensor strip (referring to the structure shown in FIG. 8) including steps as follows. Step 910 provides a first reactive film and a second reactive film. The first reactive film includes a concaved first reactive area, while the second reactive film includes a concaved second reactive area. Step 920 disposes the first reactive film on the top surface or bottom surface of the second reactive film. Step 930 forms a vent hole, which penetrates the first reactive film so as to connect the first reactive area and the second reactive area. The above-mentioned steps do not necessarily have to be in numeric order as shown in FIG. 12. For instance, the manufacturing method of the present disclosure may perform step 930 to form a vent hole in the first reactive film prior to step 920, which places the first reactive film on the second reactive film. Moreover, step 930, which forms the vent hole may include, but is not limited to, a laser ablation method to fabricate the vent hole. For example, the vent hole can be fabricated by a punch press method.

In the flow chart shown in FIG. 13, step 910, which provides the first reactive film, further includes steps as follows. Step 911 provides a substrate and step 912 is implemented. Step 912 disposes a first electrode layer on the substrate and step 913 is implemented. Step 913 forms a first insulation layer on the first electrode layer, wherein a first end of the first insulation layer is concaved to form a first reactive area with a first depth. The first insulation layer forming step 913 can be performed by coating or printing. In another embodiment (not shown), step 910, which provides the first reactive film, further includes coating or printing a first reaction layer in the first reactive area. Additionally, in accordance with other embodiments (not shown), the first insulation layer forming step 913 further includes a step that exposes an electrode of the first electrode layer, which is adjacent to a second end of the first insulation layer.

In the flow cart shown in FIG. 14, step 910, which provides the second reactive film, further includes steps as follows. Step 914 disposes a second electrode layer on the first insulation layer and step 915 is implemented. Step 915 forms a second insulation layer on the second electrode layer, wherein a first end of the second insulation layer is concaved to form a second reactive area with a second depth. The second insulation layer forming step 915 can be implemented by coating or printing. The above-mentioned steps 911 to 913 and steps 914 to 915 do not necessarily have to be in numeric order. Moreover, in another embodiment (not shown), step 910, which provides the second reactive film, further includes a step of coating or printing a second reaction layer in the second reactive area. Furthermore, in another embodiment (not shown), the second insulation layer forming step 915 further includes a step that exposes an electrode of the second electrode layer, which is adjacent to a second end of the second insulation layer.

In the flow chart shown in FIG. 15, the manufacturing method of the electrode strip (referring to the structure shown in FIG. 1) includes steps as follows. Step 1210 provides a first substrate and step 1220 is implemented. Step 1220 disposes a first electrode set on the first substrate and step 1230 is implemented. Step 1230 forms a first insulation layer on the first electrode set, wherein the first insulation layer includes a first opening and step 1240 is implemented. Step 1240 disposes a second substrate on the first insulation layer, wherein the second substrate includes a sampling opening and a connecting hole and step 1250 is implemented. Step 1250 disposes a second electrode set on the second substrate, wherein the second electrode set uncovers the connecting hole and step 1260 is implemented. Step 1260 forms a second insulation layer on the second electrode set, wherein the second insulation layer includes a second opening and the connecting hole vertically connects the first opening and the second opening. Step 1230, which forms the first insulation layer and step 1260, which forms the second insulation layer, can be performed by a coating or a printing method.

In another embodiment (not shown), the manufacturing method of the electrode strip further includes steps as follows. Step 1270 coats or prints a first reaction layer in the first opening. Step 1280 coats or prints a second reaction layer in the second opening. In addition, the above-mentioned steps 1210 to 1260 and steps 1270 to 1280 do not necessarily have to be in numeric order.

In other embodiments (not shown), the manufacturing method of the electrode strip further includes step 1290. Step 1290 disposes a cover on the second insulation layer, wherein the cover includes a through hole that connects the connecting hole. In addition, the above-mentioned steps 1210 to 1260, steps 1270 to 1280 and step 1290 do not necessarily have to be in numeric order.

Moreover, the present disclosure further provides a measurement system with hematocrit correction. The measurement system includes either the above-mentioned electrode strip or the above-identified sensor strip, and a sensor. The first electrode set or the first electrode layer is configured to measure an analyte concentration (such as the analyte concentration in the above-identified major reactive area). Either the second electrode set or the second electrode layer is configured to measure hematocrit or interfering factors in the above-mentioned minor reactive area. Moreover, the sensor is configured to electrically connect with either the electrode strip or the sensor strip. The sensor includes a power source, a detector and a microprocessor. The power source is configured to simultaneously provide a DC signal and either an AC signal or an AC with DC offset signal. The DC signal is transmitted to either the first electrode set or the first electrode layer. Either the AC signal or the AC with DC offset signal is transmitted to either the second electrode set or the second electrode layer. The detector is configured to detect a first reactive value in response to the analyte concentration and a second reactive value in response to the hematocrit concentration. The microprocessor is configured to calculate the hematocrit-corrected analyte concentration in response to the first reactive value and the second reactive value.

In the present disclosure, the sensor strip and the electrode strip can avoid cross-contamination of sample liquids in two separated reactive areas so as to be suitable for domestic usage and quick diagnosis. Although the present disclosure is disclosed in the above-identified embodiments, which do not limit the present disclosure, persons having ordinary skill in the art, without departing from the spirit and scope of the present disclosure, may modify or amend accordingly. Therefore, the protection scope of the present disclosure is based on the appended claims.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, and composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:
1. A method for manufacturing a sensor strip, comprising the steps of:
   providing a first reactive film and a second reactive film, wherein the first reactive film includes a first reactive area, and the second reactive film includes a second reactive area;
   disposing the first reactive film on the second reactive film; and
   forming a vent hole penetrating the first reactive film and connecting the first reactive area and the second reactive area,
   wherein the step of providing the first reactive film includes the following steps:
      providing a substrate;
      disposing a first electrode layer on the substrate;
      forming a first insulation layer on the first electrode layer wherein a first end of the first insulation layer is concaved to form the first reactive area within a first depth; and
      coating or printing a first reaction layer in the first reactive area, and
   wherein the step of providing the second reactive film includes the following steps:
      disposing a second electrode layer on the first insulation layer;

forming a second insulation layer on the second electrode layer wherein a first end of the second insulation layer is concaved to form the second reactive area with a second depth;
coating or printing a second reaction layer in the second reactive area; and
exposing an electrode of the second electrode layer adjacent to a second end of the second insulation layer.

2. The method for manufacturing a sensor strip according to claim 1, wherein the step of forming the first insulation layer further includes a step of exposing an electrode of the first electrode layer adjacent to a second end of the first insulation layer, and
wherein the step of forming the first insulation layer includes coating or printing.

3. The method for manufacturing a sensor strip according to claim 1, wherein the step of forming the vent hole is fabricated by a laser ablation method or a punch press method.

4. A method for manufacturing an electrode strip, comprising the steps:
providing a first substrate;
disposing a first electrode set on the first substrate;
forming a first insulation layer on the first electrode set, wherein the first insulation layer includes a first opening;
disposing a second substrate on the first insulation layer, wherein the second substrate includes a sampling opening and a connecting hole;
disposing a second electrode set on the second substrate, wherein the second electrode set uncovers the connecting hole; and
forming a second insulation layer on the second electrode set, wherein the second insulation layer includes a second opening, wherein the connecting hole vertically connects the first opening and the second opening.

5. The method for manufacturing an electrode strip according to claim 4, wherein forming the first insulation layer and the second insulation layer includes coating or printing.

6. The method for manufacturing an electrode strip according to claim 4, further comprising the steps of:
coating or printing a first reaction layer in the first opening;
coating or printing a second reaction layer in the second opening; and
disposing a cover on the second insulation layer, wherein the cover includes a through hole, and the through hole connects the connecting hole.

7. A measurement system with hematocrit correction, comprising:
an electrode strip, comprising:
a first substrate;
a first electrode set disposed directly on the first substrate;
a first insulation layer including a first opening and disposed on the first electrode set;
a second substrate disposed on the first insulation layer and including a sampling opening and a connecting hole;
a second electrode set disposed directly on the second substrate and uncovering the connecting hole; and
a second insulation layer including a second opening, wherein the connecting hole vertically connects the first opening and the second opening;
wherein the first electrode set, the first insulation layer, the second substrate, the second electrode set and the second insulation layer are disposed on one side of the first substrate;
wherein the first electrode set is configured to measure an analyte concentration, and the second electrode set is configured to measure a hematocrit concentration; and
a sensor configured to electrically connect with the electrode strip, and the sensor including:
a power source configured to simultaneously provide a direct current (DC) signal and an alternating current (AC) signal, wherein the DC signal is transmitted to either the first electrode set, and the AC signal is transmitted to either the second electrode set;
a detector configured to detect a first reactive value in response to the analyte concentration and a second reactive value in response to the hematocrit concentration; and
a microprocessor configured to calculate a hematocrit-corrected analyte concentration in response to the first reactive value and the second reactive value.

8. The measurement system with hematocrit correction according to claim 7, wherein the electrode strip further comprises a cover disposed on the second insulation layer,
wherein the cover includes a through hole connecting with the connecting hole,
wherein the second opening is located between the cover and the second substrate to form a second reactive area, and the first opening is located between the first substrate and the second substrate to form a first reactive area,
wherein the cover, the first electrode set, the first insulation layer, the second substrate, the second electrode set and the second insulation layer are disposed on the same side of the first substrate.

9. The measurement system with hematocrit correction according to claim 8, wherein the first reactive area includes a first depth, the second reactive area includes a second depth, the sampling opening includes a third depth and wherein either the first depth or the second depth is longer than the third depth, the first reactive area and the second reactive area accommodate samples from the same source, the first depth and the second depth are configured to separate the sample of the first reactive area from the sample of the second reactive area.

10. The measurement system with hematocrit correction according to claim 9, wherein an inside diameter of the first opening where the first reactive area is located is equal to an inside diameter of the sampling opening, and an inside diameter of the second opening where the second reactive area is located is equal to an inside diameter of the sampling opening.

11. The measurement system with hematocrit correction according to claim 7, wherein an inside diameter of the first opening is larger or smaller than an inside diameter of the sampling opening, and an inside diameter of the second opening is larger or smaller than an inside diameter of the sampling opening.

12. The measurement system with hematocrit correction according to claim 7, wherein an end of the second substrate, where the sampling opening is formed, is a hydrophobic surface and wherein the first insulation layer exposes a connection of the first electrode set away from the first opening, the second insulation layer exposes a connection of the second electrode set away from the second opening, and the connection of the first electrode set does not overlap with the connection of the second electrode set.

13. The measurement system with hematocrit correction according to claim 7, wherein the second substrate includes an awl-shaped end where the sampling opening is located, and the sampling opening is located at a tip area of the awl-like shaped end.

14. The measurement system with hematocrit correction according to claim 7, wherein the sampling opening is disposed at a corner of the second substrate, a lengthwise axis of the first opening and a lengthwise axis of the first insulation layer intersect to form an included angle.

15. A measurement system with hematocrit correction, comprising:
- a sensor strip, comprising:
  - a first reactive film including a substrate, a first electrode layer disposed directly on the substrate, and a first insulation layer including a first end and disposed on the first electrode layer, wherein the first end is concaved to form a first reactive area with a first depth;
  - a second reactive film including a second electrode layer disposed directly on the first insulation layer, and a second insulation layer including a first end and disposed on the second electrode layer, wherein the first end of the second insulation layer is concaved to form a second reactive area with a second depth; and
  - a vent hole penetrating the second insulation layer, the second electrode layer and the first insulation layer and connecting the first reactive area and the second reactive area;
  - wherein the first electrode layer, the first insulation layer, the second electrode layer and the second insulation layer are disposed on one side of the substrate;
  - wherein the first electrode layer is configured to measure an analyte concentration, and the second electrode layer is configured to measure a hematocrit concentration; and
- a sensor configured to electrically connect with the sensor strip and the sensor including:
  - a power source configured to simultaneously provide a direct current (DC) signal and an alternating current (AC) signal, wherein the DC signal is transmitted to the first electrode layer, and the AC signal is transmitted to the second electrode layer;
  - a detector configured to detect a first reactive value in response to the analyte concentration and a second reactive value in response to the hematocrit concentration; and
  - a microprocessor configured to calculate a hematocrit-corrected analyte concentration in response to the first reactive value and the second reactive value.

16. The measurement system with hematocrit correction according to claim 15, wherein the first end of the first insulation layer adjacent to the first electrode layer is concaved to form the first reactive area, and a sampling opening with a third depth is concaved and formed next to the first reactive area, and wherein either the first depth or the second depth is longer than the third depth and wherein the first reactive area and the second reactive area accommodate samples from an identical source and the first depth and the second depth are configured to separate the sample of the first reactive area from the sample of the second reactive area.

17. The measurement system with hematocrit correction according to claim 16, wherein an inside diameter of the first reactive area is larger or smaller than an inside diameter of the sampling opening and wherein an inside diameter of the second reactive area is larger or smaller than an insider diameter of the sampling opening and wherein the first end of the first insulation layer away from the substrate is a hydrophobic surface and wherein the first insulation layer further includes a second end, the first electrode layer includes at least one electrode, and the first insulation layer exposes the at least one electrode adjacent to the second end.

* * * * *